United States Patent [19]

Alferness

[11] Patent Number: 5,554,175
[45] Date of Patent: Sep. 10, 1996

[54] THERAPY TERMINATION IN AN ATRIAL DEFIBRILLATOR AND METHOD

[75] Inventor: Clifton A. Alferness, Redmond, Wash.

[73] Assignee: InControl, Inc., Redmond, Wash.

[21] Appl. No.: 346,500

[22] Filed: Nov. 29, 1994

[51] Int. Cl.⁶ .................................................. A61N 1/39
[52] U.S. Cl. ............................................................ 607/5
[58] Field of Search ............................................. 607/4, 5

[56] References Cited

U.S. PATENT DOCUMENTS

| | | | |
|---|---|---|---|
| 4,809,697 | 3/1989 | Causey, III et al. | 607/31 |
| 5,107,850 | 8/1992 | Olive | 607/4 |
| 5,282,837 | 2/1994 | Adams et al. | 607/4 |
| 5,314,430 | 5/1994 | Bardy | 607/5 |
| 5,350,404 | 9/1994 | Adams et al. | 607/5 |
| 5,366,486 | 11/1994 | Zipes et al. | 607/5 |
| 5,441,519 | 8/1995 | Sears | 607/5 |
| 5,464,433 | 11/1995 | White et al. | 607/5 |
| 5,470,342 | 11/1995 | Mann et al. | 607/4 |
| 5,509,925 | 4/1996 | Adams et al. | 607/5 |

FOREIGN PATENT DOCUMENTS

| | | | |
|---|---|---|---|
| 522693A1 | 1/1993 | European Pat. Off. | 607/5 |

*Primary Examiner*—William E. Kamm
*Assistant Examiner*—Carl H. Layno
*Attorney, Agent, or Firm*—Richard O. Gray, Jr.

[57] ABSTRACT

An atrial defibrillator applies cardioverting electrical energy to the atria of a heart when in need of cardioversion. The atrial defibrillator includes an atrial fibrillation detector for determining if the atria of a heart are in need of cardioversion, and a therapy sequencer for performing a therapy sequence to apply cardioverting electrical energy to the atria when the atria are in need of cardioversion. The therapy sequence is terminated when the atrial fibrillation detector fails at least twice in succession to determine that the atria are in need of cardioversion. As a result, a greater atrial fibrillation detection sensitivity is employed for terminating a therapy sequence as is employed for initiating the therapy sequence.

12 Claims, 2 Drawing Sheets

THERAPY TERMINATION IN AN ATRIAL DEFIBRILLATOR AND METHOD

BACKGROUND OF THE INVENTION

The present invention generally relates to an implantable atrial defibrillator and method for applying cardioverting electrical energy to the atria of a patient's heart in need of cardioversion. The present invention is more particularly directed to such a defibrillator which includes an atrial fibrillation detector for determining if the atria are in need of cardioversion and a therapy sequence control which terminates cardioversion therapy when the atrial fibrillation detector fails at least twice in succession to determine a need for cardioversion of the atria of the heart.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators has become a commercial reality.

Two such proposed defibrillators, although represented as being implantable, were not fully automatic, requiring human interaction for cardioverting or defibrillating the heart. Both of these proposed defibrillators required the patient to recognize the symptoms of atrial fibrillation, with one defibrillator requiring a visit to a physician to activate the defibrillator, and the other defibrillator requiring the patient to activate the defibrillator with an external magnet. Neither defibrillator included an atrial fibrillation detector or detected atrial activity of the heart. As a result, these manually operated defibrillators provided no atrial fibrillation detection support for the patient.

An improved implantable atrial defibrillator which is automatic in operation is fully described in U.S. Pat. No. 5,282,837. The atrial defibrillator disclosed in this patent is truly automatic by including an atrial fibrillation detector which, responsive to sensed atrial activity, determines when the atria of the heart are in need of cardioversion. When the atrial fibrillation detector determines that the atria are in fibrillation and thus in need of cardioversion, the atrial fibrillation detector causes a cardiovertor stage to deliver defibrillating or cardioverting electrical energy to the atria in time relation to a detected ventricular electrical activation (R wave) of the heart. As a result, the atria are automatically and safely cardioverted.

Atrial fibrillation, unlike ventricular fibrillation, is generally not immediately life threatening. As a result, once atrial fibrillation is detected, a therapy sequence may be initiated which provides for delivery of a number of cardioverting shocks having peak voltages which incrementally increase from a relatively low level to eventually a relatively high level. Therapy may then be terminated as soon as the atrial fibrillation detector confirms successful cardioversion. Such a therapy sequence preferably includes detection for atrial fibrillation prior to each shock to be delivered and after each shock is delivered. This sequence may continue until a predetermined number of cardioversion attempts have been made.

While it is, of course, beneficial to the patient for the atrial fibrillation detector to detect for atrial fibrillation prior to and after each attempted cardioversion, such repeated detection can cause a problem of its own. No fibrillation detector is one hundred percent accurate (one hundred percent sensitivity with one hundred percent specificity) in determining if there is a need for cardioversion. Hence, if numerous detections are required in a therapy sequence, due to numerical probabilities, there will be some finite possibility that the detector will fail to detect the need for further cardioversion and terminate the therapy when there actually exists a need for further cardioversion. The end result of this would be that the fibrillation would not be successfully cardioverted and would persist.

The present invention provides a simple, yet elegant solution to this problem. To accomplish this end, the present invention provides an atrial defibrillator and method wherein a therapy sequence is initiated upon a first detection of atrial fibrillation with a first sensitivity, and wherein the therapy sequence is terminated when the atrial fibrillation detector, with a second and greater sensitivity, fails to detect a need for further cardioversion. The sensitivity of the detector is thus increased after therapy is initiated to significantly reduce the probability that the presence of atrial fibrillation will go undetected during a therapy sequence.

SUMMARY OF THE INVENTION

The present invention provides an atrial defibrillator including therapy means for performing a therapy sequence to apply cardioverting electrical energy to the atria when the atria are in need of cardioversion, and an atrial fibrillation detector for determining if the atria of a heart are in need of cardioversion. The atrial fibrillation detector has a first sensitivity and a second sensitivity for detecting when the atria are in need of cardioversion, with the second sensitivity being greater than said first sensitivity. The atrial defibrillator further includes means for causing the atrial fibrillation detector to determine with the first sensitivity if the atria are in need of cardioversion for initiating the therapy sequence, and to determine with the second sensitivity if the atria are in need of cardioversion for terminating the therapy sequence.

The present invention also provides an atrial defibrillator including an atrial fibrillation detector for determining if the atria of a heart are in need of cardioversion, therapy means for performing a therapy sequence to apply cardioverting electrical energy to the atria when the atria are in need of cardioversion, and means for terminating the therapy sequence when the atrial fibrillation detector fails at least twice in succession to determine that the atria are in need of cardioversion.

The present invention further provides an atrial defibrillator for applying cardioverting electrical energy to the atria of a heart when in need of cardioversion. The atrial defibrillator includes sensing means for sensing atrial activity of the heart, an atrial fibrillation detector responsive to sensed atrial activity for determining when cardioversion is needed, and initiating means for initiating a cardioversion therapy sequence. The atrial defibrillator further includes therapy sequence control means for controlling the cardioversion therapy sequence. The therapy sequence control means provides a first command to the atrial fibrillation detector, during the sequence, to cause the atrial fibrillation detector to determine if cardioversion is needed, provides a second command to the atrial fibrillation detector to cause the atrial fibrillation detector to determine if cardioversion is needed responsive to the atrial fibrillation detector failing to determine a need for cardioversion in response to the first command, and terminates the sequence in response to the atrial fibrillation detector failing to determine a need for cardioversion in response to both the first and second commands.

The present invention still further provides a method of providing cardioverting therapy to the atria of a heart. The method includes the steps of sensing atrial activity of the heart, detecting from the sensed atrial activity with a first sensitivity if the atria are in need of cardioversion, and initiating a therapy sequence upon detecting that the atria are in need of cardioversion. The therapy sequence includes applying cardioverting electrical energy to the atria of the heart, redetecting with a second sensitivity if the atria are in need of cardioversion, and terminating the therapy sequence after the redetecting step if the atria are not in need of cardioversion. The second sensitivity is greater than the first sensitivity.

The present invention still further provides a method of providing cardioverting therapy to the atria of a heart. The method includes the steps of sensing atrial activity of the heart, detecting from the sensed atrial activity if the atria are in need of cardioversion, and initiating a therapy sequence upon detecting that the atria are in need of cardioversion. The therapy sequence includes the steps of applying cardioverting electrical energy to the atria of the heart, determining if the atria are in need of cardioversion, and redetermining if the atria are in need of cardioversion if the determining step fails to determine a need for cardioversion. The method further includes the step of terminating the therapy sequence if the redetermining step fails to determine a need for cardioversion.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
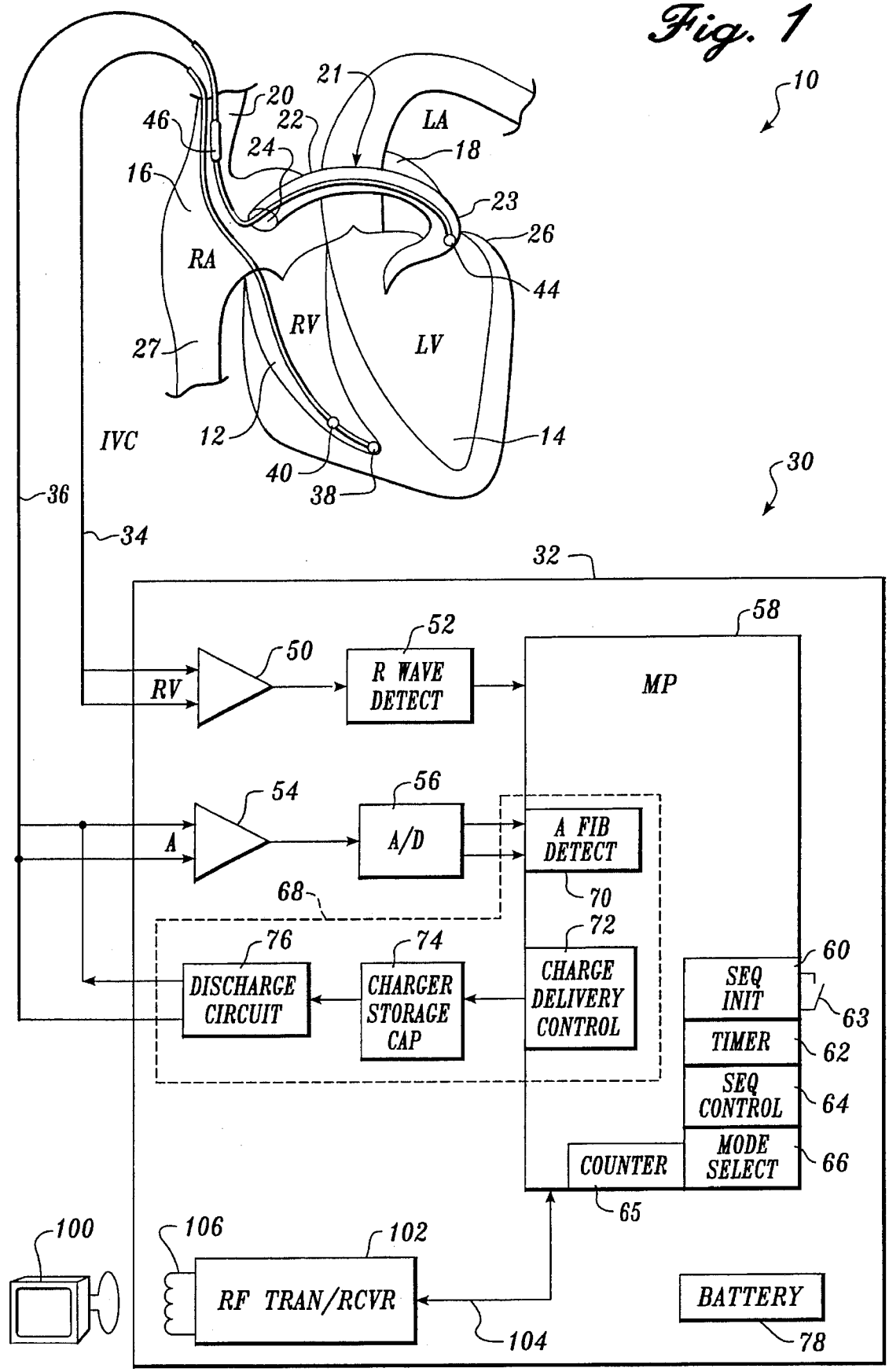
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria; and, FIG. 2 is a flow diagram illustrating the manner in which the atrial defibrillator of FIG. 1 may be implemented to provide a therapy sequence which is terminated in accordance with a preferred embodiment of the present invention.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16 and then into the right ventricle 12, as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16.

The first electrode 44 together with the second electrode 46 provide bi-polar sensing of heart activity in the atria 16 and 18. The first electrode 44 and the second electrode 46 further provide for the delivery of defibrillating or cardioverting electrical energy to the atria.

Within the enclosure 32, the atrial defibrillator 30 includes a first sense amplifier 50, an R wave detector 52, and a second sense amplifier 54. The first sense amplifier 50 and the R wave detector 52, together with electrodes 38 and 40 of lead 34, sense ventricular activations of the right ventricle 12. The second sense amplifier 54, together with the first electrode 44 and second electrode 46 of the second lead 36, detect atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog-to-digital convertor 56 which converts the analog signal representative of the atrial activity of the heart being detected to digital samples for further processing in a manner to be described hereinafter.

The enclosure 32 of the atrial defibrillator 30 further includes a microprocessor 58. The microprocessor 58 is preferably implemented in a manner as described in U.S. Pat. No. 5,282,837, or as described in U.S. Pat. No. 5,350,404, and further as described hereinafter with respect to the flow diagram of FIG. 2. The implementation of the microprocessor 58 in accordance with this embodiment of the present invention results in a plurality of functional stages. The stages include a therapy sequence initiating stage 60, a timer 62, a therapy sequence control stage 64, a counter 65, a mode select stage 66, an atrial fibrillation detector 70, and a charge and delivery control stage 72.

The microprocessor 58 is arranged to operate in conjunction with a memory (not shown) which may be coupled to the microprocessor 58 by a multiple-bit address bus (not shown) and a bi-directional multiple-bit data bus (not shown). This permits the microprocessor 58 to address desired memory locations within the memory for executing write or read operations. During a write operation, the microprocessor stores data and operating parameters (such as a selected modality) in the memory at the addresses defined by multiple-bit addresses conveyed over the address bus and conveys the data to the memory over the multiple-bit data bus. During a read operation, the microprocessor 58 obtains data from the memory at the storage locations identified by the multiple-bit addresses provided over the address bus and receives the data from the memory over the bi-directional data bus.

For entering operating parameters into the microprocessor 58, such as mode selection, the microprocessor 58 receives programmable operating parameters, such as mode commands, from an external controller 100 which is external to the skin of the patient. The external controller 100 is arranged to communicate with a receiver/transmitter 102 which is coupled to the microprocessor 58 over a bi-directional bus 104. The receiver/transmitter 102 may be of the type well known in the art for conveying various information which it obtains from the microprocessor 58 to the external controller 100 or for receiving programming parameters, such as mode commands, from the external controller 100 which the receiver/transmitter 102 then conveys to the microprocessor 58 for storage in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One such communication system is disclosed, for example, in U.S. Pat. No. 5,342,408, which is incorporated herein by reference.

The atrial defibrillator 30 further includes an intervention sequencer 68 which performs an intervention sequence, including atrial fibrillation detection and cardioversion of the atria (if necessary). To that end, the intervention sequencer includes the previously mentioned atrial fibrillation detector 70 and charge and delivery control 72, and a charger and storage capacitor circuit 74 and a discharge circuit 76.

Each intervention sequence is begun by the sequence initiating stage 60. When the defibrillator 30 is programmed in an automatic mode, the sequence initiating stage 60 initiates an intervention sequence at spaced apart times which are preferably determined by the timer 62. When the defibrillator is programmed in a patient activated mode, the sequence initiating stage 60 initiates an intervention sequence when a sequence command generated external to the patient is received by a sequence command receiver, preferably formed by a read switch 63. The sequence command, in accordance with this preferred embodiment, is a magnetic field generated by a magnet of the type well now in the art which is brought into close proximity with the implanted defibrillator 30. When the intervention sequencer 68 is not performing an intervention sequence, it is held in a deactivated or inactive state by the sequence control stage 64. When an intervention sequence is to be performed, the sequence initiating stage 60 overrides the sequence control stage 64 to cause the intervention sequencer to perform an intervention sequence.

Each intervention sequence preferably begins with the atrial fibrillation detector 70 determining if the atria are in need of cardioversion. This analysis is preferably performed on data obtained from sense amplifier 54 and analog-to-digital convertor 56, which is prestored in the aforementioned memory (not shown) external to the microprocessor 58, but contained within the implantable enclosure 32. The atrial fibrillation detector 70 may alternatively be of the type which performs real time analysis of the data provided by the analog-to-digital convertor 56. Lastly, the defibrillator 30 includes a depletable power source 78, such as a lithium battery. The battery 78, of course, provides power to the electrical components of the atrial defibrillator 30.

If the atrial fibrillation detector determines that the atria are in fibrillation, and hence in need of cardioversion, the intervention sequencer 68, under control of the sequence control stage 64, enters a therapy sequence to cardiovert the atria.

The operation of the atrial defibrillator 30 in performing the cardioversion therapy sequence will now be described in connection with the flow diagram of FIG. 2.

Figure 2:
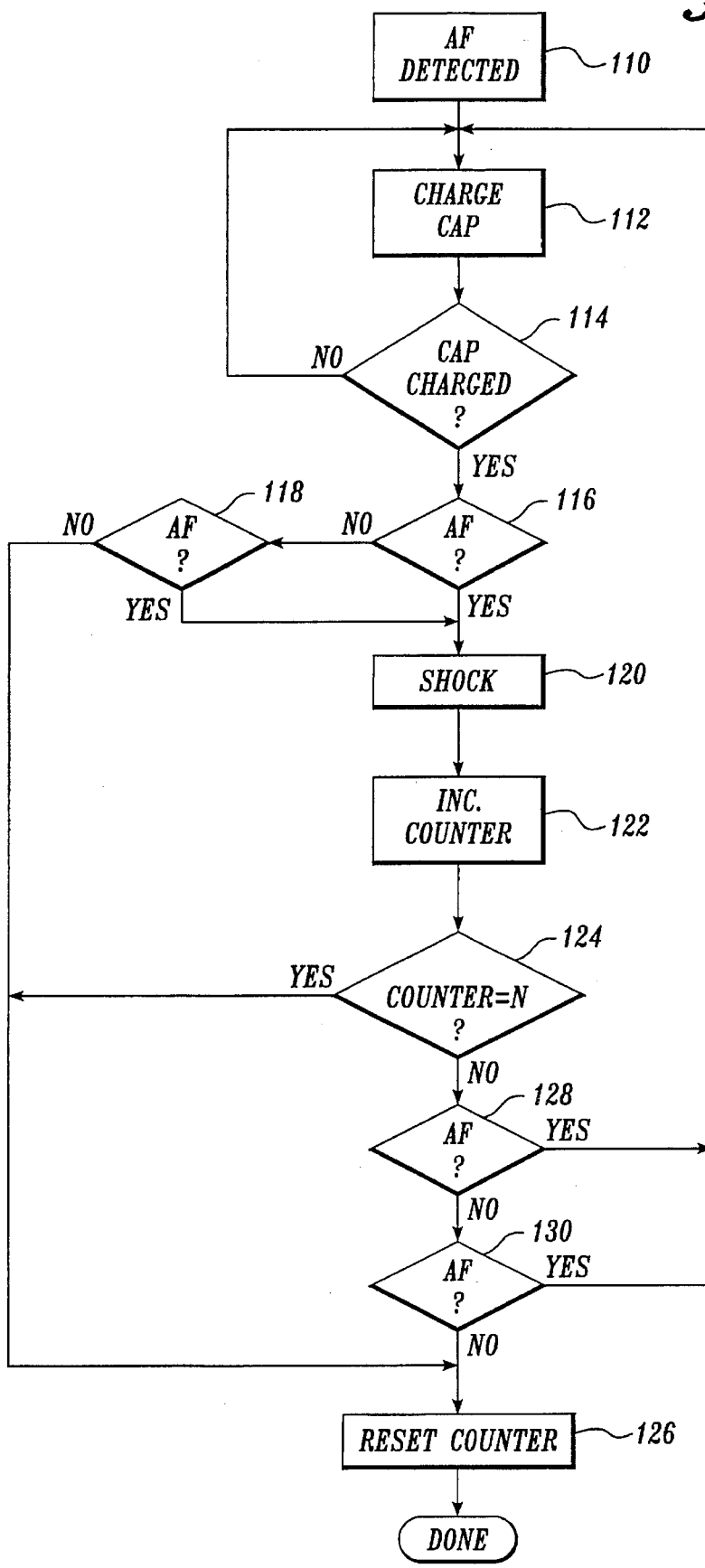

Referring now to FIG. 2, the atrial defibrillator 30 enters the therapy sequence upon the atrial fibrillation detector 70 determining that the atria are in fibrillation and in need of cardioversion as denoted by step 110. Next, in step 112, the charger and storage capacitor circuit 74 under control of the charge and delivery stage 72 charges its storage capacitor to a predetermined voltage level for cardioverting the atria of the patient's heart. When the capacitor of circuit 74 is charged, as determined in step 114, the sequence control 64 provides a first command to the atrial fibrillation detector 70 to cause the atrial fibrillation detector to determine if the atria are in need of cardioversion in step 116. If the atrial fibrillation detector 70 determines that the atria are not in fibrillation, the sequence control provides a second command to the atrial fibrillation detector 70 to cause the atrial fibrillation detector to once again determine if the atria are in need of cardioversion in step 118. If the atrial fibrillation detector 70 once again, for a second successive time, determines that the atria are not in need of cardioversion, the sequence control 64 will terminate the therapy sequence in a manner to be describe subsequently. However, if it is determined in either of steps 116 or 118 that the atria are in need of cardioversion, the sequence control 64 enables the charge and delivery control stage 72 to cause the discharge circuit in step 120 to discharge the storage capacitor within circuit 74 for a predetermined time to provide a controlled discharge of cardioverting electrical energy to the atria of the heart. To that end, the discharge circuit 76 is coupled to the first electrode 44 and the second electrode 46 of the second lead 36 for applying the cardioverting or defibrillating electrical energy to the atria. The discharge is preferably initiated in timed relation to an R wave detected by sense amplifier 50 and R wave detector 52. Interval timing prior to energy delivery is also preferably performed as taught in U.S. Pat. No. 5,207,219.

After the cardioverting electrical energy is applied to the atria in step 120, the sequence control 64 next, in step 122, causes the counter 65 to be incremented. The counter 65 keeps track of the number of attempted cardioversions. Next, in step 124, the defibrillator 30 determines if the count in counter 65 is equal to a predetermined maximum number of counts previously stored in the defibrillator, as described earlier. If the count in counter 65 does equal the predetermined count, the sequence control 64 next terminates the therapy. The therapy is terminated by resetting counter 65 in step 126 and exiting the therapy sequence. As previously mentioned, the therapy is terminated in this manner after step 118 wherein it was determined for the second successive time that the atria were not in need of cardioversion.

If the count in counter 65 does not equal the maximum count, the atrial fibrillation detector 70 once again, under command from the sequence control 64, determines if the atria are in fibrillation in accordance with step 128. If the atria are still in fibrillation, the sequence control 64 returns to step 112 to once again charge the storage capacitor to an incrementally increased voltage level in anticipation of again applying cardioverting electrical energy to the atria of the heart. However, if in step 128 the atrial fibrillation detector 70 fails to detect atrial fibrillation, the atrial fibrillation detector 70 is once again immediately called upon in step 130 to detect for atrial fibrillation under command of the sequence control 64. If the atria are now found to be in fibrillation, the sequence control 64 returns to step 112 to charge the capacitor to prepare for the next application of cardioverting electrical energy to the atria.

If the atrial fibrillation detector 70 determines in step 130 that the atria are not in fibrillation, the atrial fibrillation episode will be considered to have been terminated by the last cardioversion. The process thus returns after the counter 65 is reset.

Hence, as can be seen from the foregoing, once atrial fibrillation is first detected in step 110 with a first sensitivity, the sequence control continuously applies cardioverting electrical energy to the atria of the heart until either the heart is successfully cardioverted or until the number of cardioversion attempts equals a preselected specific number of such attempts. Hence, the therapy is terminated before that number of attempts have been counted only if the atrial fibrillation detector fails, with a second and greater sensitivity, to determine that the atria are in need of cardioversion. In accordance with this preferred embodiment, the second and greater sensitivity is achieved by causing the atrial fibrillation detector to redetect a second time in succession for a need to cardiovert the atria if a first detect fails to detect such a need. Hence, as illustrated in steps 116, 118 and 128, 130, the greater sensitivity is obtained after the therapy sequence is initiated. For example, if the atrial fibrillation detector has a sensitivity of 0.98, it will have an effective sensitivity of 0.98+(0.02×0.98)=0.9996 when performing two successive detects for the absence of atrial fibrillation.

While a particular embodiment of the present invention has been shown and described, modifications may be made. For example, separate atrial fibrillation detectors, having different sensitivities, may be employed without departing from the present invention. With such an implementation, the detector having the lesser sensitivity of, for example, 0.98, may be employed for initiating the therapy sequence, and the other detector, having a greater sensitivity of, for example, 0.9996, may be employed during the therapy sequence to terminate the therapy sequence. Hence, it is therefore intended in the appended claims to cover all such changes and modifications which fall within the true spirit and scope of the invention.

What is claimed is:

1. An atrial defibrillator comprising:

therapy means for performing a therapy sequence including cardioverting the atria of a human heart when the atria are in need of cardioversion;

an atrial fibrillation detector for determining if the atria of the heart are in need of cardioversion, the atrial fibrillation detector having a first sensitivity and a second sensitivity for detecting when the atria are in need of cardioversion, said second sensitivity being greater than said first sensitivity;

means for causing said atrial fibrillation detector to determine with said first sensitivity if the atria are in need of cardioversion;

means for initiating said therapy sequence if the atrial fibrillation detector detects with the first sensitivity that the atria are in need of cardioversion;

second means for causing said atrial fibrillation detector during said therapy sequence to determine with said second sensitivity if the atria are still in need of cardioversion; and means for terminating said therapy sequence if the atrial fibrillation detector fails to detect with the second sensitivity that the atria are still in need of cardioversion.

2. An atrial defibrillator comprising:

an atrial fibrillation detector for determining if the atria of a heart are in need of cardioversion;

therapy means for performing a therapy sequence to apply cardioverting electrical energy to the atria when the atria are in need of cardioversion; and, means for terminating the therapy sequence when the atrial fibrillation detector fails at least twice in succession to determine that the atria are in need of cardioversion.

3. An atrial defibrillator for applying cardioverting electrical energy to the atria of a heart when in need of cardioversion, said atrial defibrillator comprising:

sensing means for sensing atrial activity of the heart;

an atrial fibrillation detector responsive to the sensing means for determining when cardioversion is needed;

initiating means for initiating a cardioversion therapy sequence; and, therapy sequence control means for controlling said cardioversion therapy sequence and providing therapy sequence control commands including a cardioversion command; a first command to the atrial fibrillation detector, during said sequence, to cause the atrial fibrillation detector to determine if cardioversion is needed, and a second command to the atrial fibrillation detector to cause the atrial fibrillation detector to determine if cardioversion is needed responsive to the atrial fibrillation detector failing to determine a need for cardioversion in response to the first command; and a cardiovertor for applying the cardioverting electrical energy to the atria in response to said therapy sequence control means providing the cardioversion command, wherein said therapy sequence control means provides the first command prior to providing the cardioversion command and further includes means for terminating said sequence in response to the atrial fibrillation detector failing to determine a need for cardioversion in response to both the first and second commands.

4. An atrial defibrillator as defined in claim 3 wherein said therapy sequence control means provides the second command to the atrial fibrillation detector immediately after the atrial fibrillation detector fails to determine a need for cardioversion in response to the first command.

5. An atrial defibrillator as defined in claim 3 wherein said therapy sequence control meansincludes means for repeatedly providing a cardioversion command to said cardiovertor and means for providing the first command after each application of cardioverting electrical energy to the atria by the cardiovertor.

6. A method of providing cardioverting therapy to the atria of a heart, the method including the steps of:

sensing atrial activity of the heart;

detecting from the sensed atrial activity with a first sensitivity if the atria are in need of cardioversion; and, initiating a therapy sequence upon detecting that the atria are in need of cardioversion, the therapy sequence including applying cardioverting electrical energy to the atria of the heart, redetecting with a second sensitivity if the atria are in need of cardioversion, and terminating said therapy sequence after the redetecting step if the atria are not in need of cardioversion, said second sensitivity being greater than said first sensitivity.

7. A method of providing cardioverting therapy to the atria of a heart, the method including the steps of:

sensing atrial activity of the heart;

detecting from the sensed atrial activity if the atria are in need of cardioversion;

initiating a therapy sequence upon detecting that the atria are in need of cardioversion, the therapy sequence including applying cardioverting electrical energy to the atria of the heart, determining if the atria are in need of cardioversion, and redetermining if the atria are in need of cardioversion if the determining step fails to determine a need for cardioversion; and, terminating the therapy sequence if the redetermining step fails to determine a need for cardioversion.

8. A method as defined in claim 7 wherein said determining and redetermining steps are performed prior to said applying step.

9. A method as defined in claim 7 wherein said determining and redetermining steps are performed after said applying step.

10. A method as defined in claim 7 wherein said determining and redetermining steps are performed before said applying step and are repeated after said applying step.

11. A method as defined in claim 7 wherein said redetermining step is performed immediately after said determining step.

12. In an atrial defibrillator which initiates therapy intervention upon initial detection of fibrillation of the atria and which terminates the therapy intervention upon detection of an absence of atrial fibrillation after initiation of therapy intervention, an atrial fibrillation detector comprising:

a processor for analyzing cardiac data under control of a first atrial fibrillation detection algorithm to initially detect atrial fibrillation and initiate therapy intervention; and means for causing the processor to analyze cardiac data under control of a second atrial fibrillation detection algorithm to detect the absence of atrial fibrillation after the initial detection of atrial fibrillation;

wherein the second atrial fibrillation detection algorithm is different than the first atrial fibrillation detection algorithm.

* * * * *